US 6,646,159 B2

(12) United States Patent
Baird et al.

(10) Patent No.: US 6,646,159 B2
(45) Date of Patent: Nov. 11, 2003

(54) CARBONYLATION PROCESS

(75) Inventors: Lance A. Baird, Prospect Heights, IL (US); Leonid B. Galperin, Wilmette, IL (US); R. Joe Lawson, Arlington Heights, IL (US); Robert H. Jensen, Hinsdale, IL (US); Oleg L. Eliseev, Lubertsy (RU); Albert L. Lapidus, Moscow (RU); Aduard G. Ostapenco, Moscow (RU)

(73) Assignee: UOP LLC, Des Plaines, IL (US)

( * ) Notice: Subject to any disclaimer, the term of this patent is extended or adjusted under 35 U.S.C. 154(b) by 355 days.

(21) Appl. No.: 09/746,585

(22) Filed: Dec. 21, 2000

(65) Prior Publication Data

US 2002/0019562 A1 Feb. 14, 2002

Related U.S. Application Data

(60) Provisional application No. 60/173,525, filed on Dec. 29, 1999.

(51) Int. Cl.$^7$ .................. C07C 51/114; C07C 67/36; C07C 67/38; C07C 5/373
(52) U.S. Cl. .................. 562/521; 562/522; 560/232; 560/233; 585/654; 585/655
(58) Field of Search .................. 562/521, 522; 585/654, 655; 560/232, 233

(56) References Cited

U.S. PATENT DOCUMENTS

| 4,523,045 A | * | 6/1985 | Vora | |
|---|---|---|---|---|
| 4,960,926 A | | 10/1990 | Drent | 560/233 |
| 5,254,720 A | | 10/1993 | Wu | 560/105 |
| 5,731,255 A | | 3/1998 | Pan et al. | 502/155 |
| 5,866,716 A | | 2/1999 | Schafer et al. | 562/522 |
| 5,869,738 A | | 2/1999 | Pan et al. | 560/207 |
| 5,981,796 A | | 11/1999 | Breed et al. | 562/521 |

FOREIGN PATENT DOCUMENTS

GB              684958 A    * 12/1952

OTHER PUBLICATIONS

Fenton, D.M. *J.Org. Chem.*, vol. 38, No. 18 (1973) p. 3192–3198.
Knifton, J.F. *J.Org. Chem.*, vol. 41, No. 17 (1976) p. 2885–2890.
Hofmann P. et al. *Ind. Eng. Chem. Prod. Res. Dev.*, (1980), 19, pp. 330–334.
Drent, E. et al. *Journal of Organometallic Chemistry*, 455 (1993) pp. 247–253.

* cited by examiner

Primary Examiner—Samuel Barts
Assistant Examiner—Paul A. Zucker
(74) Attorney, Agent, or Firm—John G. Tolomei; Frank S. Molinaro; Maryann Maas

(57) ABSTRACT

Long chain alcohols and acids or other similar oxygenates such as esters are produced from paraffins of similar carbon number by a process comprising paraffin dehydrogenation, carbonylation, and separation. Preferably a mixture of paraffins extending over several carbon numbers and recovered from a kerosene fraction is processed, and unconverted paraffins are recycled to a dehydrogenation zone. Alternative reaction zone configurations, catalyst systems and product recovery methods are disclosed.

30 Claims, 2 Drawing Sheets

CARBONYLATION PROCESS

This application claims the benefit of the filing date of Provisional application 60/173,525 filed Dec. 29, 1999.

FIELD OF THE INVENTION

The invention relates to a hydrocarbon conversion process in which carboxylic acids or esters are produced by reaction of carbon monoxide and water or an alcohol with a hydrocarbon chain substrate such as an olefinic hydrocarbon. More specifically, the invention relates to a multi-step process for the production of carboxylic acids from straight or branched long chain paraffins by sequential dehydrogenation and carbonylation.

RELATED ART

The production of carboxylic acids by the carbonylation of the corresponding olefin is a well described in the art and is also practiced commercially, although primary for the production of low molecular weight acids such as acetic acid.

The use of a palladium based carbonylation catalyst is described in a paper at page 3192 of *J. Org. Chem.*, Vol. 38, No. 18, 1973 by D. M. Fenton. This reference describes the effects of a number of variables including temperature, additional reagents, solvents, and the identity of the phosphine substituents of the palladium-phosphine complex used as the catalyst. A similar paper by J. F. Knifton at page 2885 of *J Org. Chem.*, Vol. 41, No. 17, 1976 describes the production of carboxylic acid esters from linear α olefins using a ligand-stabilized platinum(II)-group 4B metal halide catalyst exemplified by $[(C_6H_5)_3P]_2PdCl_2$—$SnCl_2$. This reference reports the result of using a variety of palladium complexes and reported the performance of the catalyst system varied with the coordinated ligands. The reference also indicates that internal, disubstituted olefins carbonylate more slowly than linear olefins and produce a different product distribution.

Another interesting reference is the Hoffman et. al. paper (*Ind. Eng Chem. Prod. Res. Dev.*, 1980, 19, 330–334) which describes the examination of 300 combinations of nonnoble group 8 metals and halogen-free promoters as catalysts for carbonylation. An apparent optimum catalyst system of cobalt/pyridine or γ-picoline and αoctene was used to study the affects of various parameters on the carbonylation of a mixture of isomeric internal n-dodecenes. This reference describes the usage of hydroformylation to produce fatty acids and "fatty type" alcohols and indicated carbonylation had not yet been used to produce fatty acid esters or alcohols commercially. The reference includes, as FIG. 8, a suggested process flow for the recovery of the product acid esters of a carbonylation process.

U.S. Pat. No. 4,960,926 issued to E. Drent describes another catalyst system for carbonylation comprising a homogeneous palladium catalyst, an organic phosphine, a non-carboxylic or non-halogen acid of set character, a promoter and a catalyst stabilizer. The reference indicates the unsaturated compounds in the feed stream which are converted in the reaction can be cycloalkenes. A paper by E. Drent, et al published at pages 247–253 of the *Journal of Organometallic Chemistry*, 455 (1993) describes the effects of different ligand structures and acid types in what appears to be a similar catalyst system.

U.S. Pat. No. 5,254,720 issued to T. Wu describes a process for producing aliphatic carboxylic acids or their alkyl esters using a catalyst system comprising palladium and copper compounds, at least one acid stable ligand, and an acid such as hydrochloric acid. This reference also indicates an optional solvent may be present in the reaction zone and lists as possible solvents a variety of ketones including acetone and aromatic hydrocarbons including xylenes. U.S. Pat. No. 5,869,738 issued to L. R. Pan et al. describes another carbonylation catalyst system comprising a Group VIII metal such as palladium or palladium chloride supported on a carrier, a ligand such as triphenylphosphine and an acid such as an alkyl sulfonic acid. The reaction may be carried out in an inert organic solvent. Mentioned solvents include an aliphatic hydrocarbon e.g. octane, an aromatic hydrocarbon such as benzene or a halogenated hydrocarbon such as chloroform or a mixture of these.

The use of nitrogen-containing heterocyclic compounds as a carbonylation catalyst component is known in the art. For instance, U.S. Pat. No. 5,866,716 issued to M. Schafer et al. describes a catalyst system based upon a halogen-free rhodium compound and a nitrogen-containing heterocyclic compound such as pyridine, quinoline or imidazole.

U.S. Pat. No. 5,981,796 issued to A. J. M. Breed, et al, describes a process for the manufacture of what are characterized as trialkylacetic acids having from 5 to 19 carbon atoms per molecule by the reaction of a branched olefin with carbon monoxide and water in the presence of a heterogeneous catalyst. The use of a resin type catalyst having sulfonic groups is preferred, but the use of a zeolitic catalyst is also referred to. The reference indicates the process can be practiced in a continuously backmixed reactor such as a stirred tank rector (CSTR), fluidized reactor or recycle reactor.

It is known in the art of catalytic reforming to contact the feed stream fed to a pilot plant with sodium in order to remove sulfur from the feed stream.

BRIEF SUMMARY OF THE INVENTION

The invention is a continuous process for the conversion of long chain aliphatic paraffins to oxygenate hydrocarbons such as organic acids and alcohols via carbonylation (hydrocarboxymethylation). The invention also includes a unique carbonylation method which employs a multicomponent homogeneous catalyst system.

The invention may be characterized as a continuous process for the production of oxygenated hydrocarbons which comprises passing a feed stream comprising at least two different paraffinic hydrocarbons, each having a carbon number above 6, into a dehydrogenation zone operated at dehydrogenation conditions and converting a least a portion of the entering paraffinic hydrocarbons to olefinic hydrocarbons of the same carbon number to form a dehydrogenation zone effluent stream comprising a mixture of olefinic and paraffinic hydrocarbons; passing at least a portion of the hydrocarbons of said dehydrogenation zone effluent stream, carbon monoxide and a nucleophile supplying feed, preferably a hydroxyl-supplying feed compound chosen from water and a light alcohol, into contact with a homogeneous carbonylation catalyst in a carbonylation zone operated at carbonylation conditions and converting at least a portion of said olefinic hydrocarbons to desired carbonylation products, and recovering a product stream comprising carbonylation products and paraffinic hydrocarbons from the carbonylation zone; passing said product stream into a fractional distillation zone in which the product stream is separated into at least a hydrocarbon recycle stream comprising paraffinic hydrocarbons and an oxygenate stream comprising carbonylation products; recycling the hydrocarbon recycle stream to the dehydrogenation zone; recovering the carbonylation products.

Another embodiment of the invention may be characterized as a carbonylation process which comprises passing water, carbon monoxide and a $C_8$-plus aliphatic substrate having a carbonylizable double bond, such as an alkene, ester or alcohol into a carbonylation reaction zone maintained at carbonylation conditions and into contact with a homogeneous carbonylation catalyst system comprising either palladium and imidazole or a Pd $(PPh_3)_2$ complex, an aliphatic organic acid and a solvent to produce corresponding carboxylic acids, and recovering said carboxylic acids from the carbonylation reaction zone.

The subject process is capable of achieving greater than 95% conversion of a long chain olefin, such as 1-dodecene at greater than 95% selectivity to a carboxylic acid which contains at least 50% linear products (1-tridecanoic acid).

DETAILED DESCRIPTION AND PREFERRED EMBODIMENTS

Figure 1:
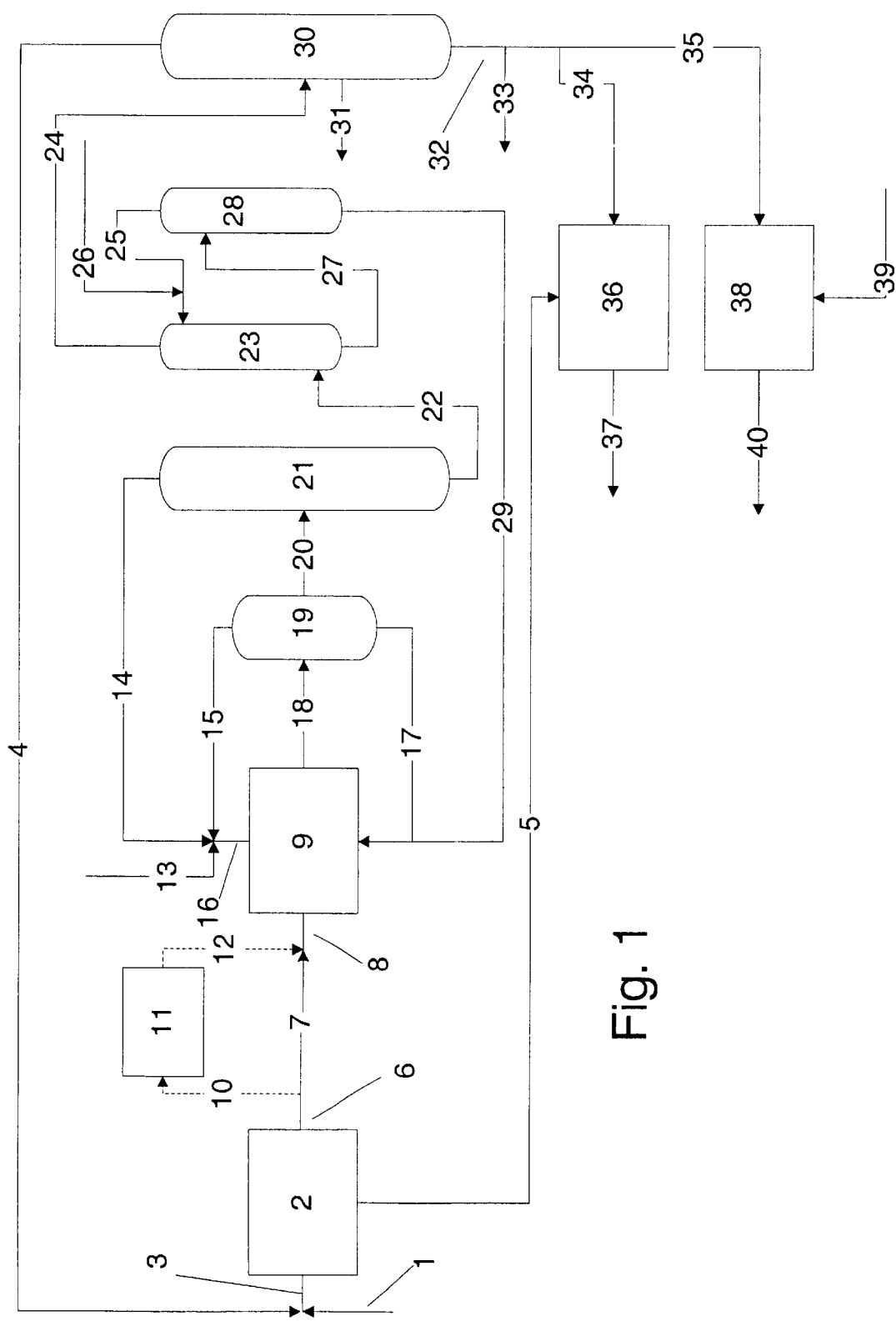
FIG. 1 is a simplified flow diagram of a process for the production of carboxylic acids from paraffinic hydrocarbons using a dehydrogenation zone and a carbonylation zone in sequence.

Long chain organic acids and alcohols have utility both as useful compounds and as intermediates or precursors to other useful compounds. As used herein the term "long chain" is intended to refer to acyclic compounds having seven or more carbon atoms per molecule. For instance, long chain alcohols are used as plasticizers and in the production of synthetic detergents. Long chain acids have similar usage in producing consumer products such as cleaning products and in producing a variety of industrial chemicals. The long chain acids of the subject invention include the widely used "fatty acids". Fatty acids derived from the saponification of fats and oils were once a major source of soap. They were displaced by a variety of synthetic detergents and cleaners formulated from linear alkyl benzene sulfonates (LAS) due to such factors as greater detergency, sudsing qualities and biodegradability. Recently, interest has returned to the use fatty acids in the production of soap, detergent, cleaners, clothing softeners and other products as described in WIPO publication number 92/20722 (international application No. PCT/US98/22054). The preferred soap and detergent materials according to this reference appear to be midchain branched fatty acids. This reference is incorporated herein for its teaching in respect to the preferred fatty acids for specific consumer product applications, downstream techniques for the conversion of fatty acids into these consumer products, and for suitable product formulations including suitable additional ingredients such as perfumes, scum suppressors and brighteners. Fatty acid derivatives may be employed by themselves as cleaning compounds or in combination with other compounds including polyhydroxy fatty acid amides, sulfated fatty acid amides or alkyl ethoxy carboxylates as described in U.S. Pat. No. 5,736,503.

It is an objective of this invention to provide a process for the production of long chain saturated carboxylic acids e.g., stearic acid or palmitic acid, or long chain alcohols. It is another objective of the subject invention to provide an improved process to produce $C_{10}$-plus straight or branched chain carboxylic acids, esters or amides which may used in the production of consumer products such as soaps and detergents. These desired product compounds include branched fatty acids chosen from compounds referred to as decanoic acid; undecanoic acid; dodecanoic acid; tridecanoic acid (TDA); tetradecanoic acid; pentadecanoic acid; hexadecanoic acid; heptadecanoic acid; and nonadecanoic acid. Specific examples of the fatty acids which are included within these objectives are 2-methyl lauric acid, 2,3- and 2,4-dimethyldecanoic acids; 2,4,5-trimethyldecanoic acid; 2,4,6-trimethyldecanoic acid; 2-propyldecanoic acid and 3,4-dimethyl-2-ethylundecanoic acid.

The subject invention achieves these objectives by the use of a unique flow scheme that includes paraffin dehydrogenation, olefin carbonylation using a homogeneous catalyst, and specific product recovery/catalyst recycle steps. This flow scheme is enhanced by unique catalytic and reaction zone technology.

The overall process flow of one embodiment of the subject invention can be best ascertained by reference to the Drawing. FIG. 1 is a simplified flow diagram which only shows main flows of this one embodiment of the invention. The figure does not show the many pieces of ancillary equipment required for performing the process such as valves, controls, sensors, pumps and drag stream removal lines which may be of customary design. In this embodiment a paraffin feed stream comprising a mixture of straight chain $C_{10}$–$C_{13}$ paraffins enters the process through line 1. The paraffin feed stream is admixed with a recycle hydrocarbon stream from line 4 and passed into the dehydrogenation zone 2 via line 3. The entering mixture of hydrocarbons is therein contacted with a bed of a solid dehydrogenation catalyst at dehydrogenation conditions effective to promote the conversion of an acceptable percentage of the entering paraffins into the corresponding olefins. Included within the dehydrogenation zone 2 are the requisite facilities, of a conventional nature, to separate the effluent of the catalyst into an off gas stream comprising hydrogen produced in the process and an effluent stream rich in a admixture of the product and the feed hydrocarbons. As used herein the term "rich" is intended to indicate a concentration of the specified compound or class of compounds greater than 50 and preferably greater than 70 mole percent.

At the present time conversion of higher hydrocarbons to the corresponding olefinic hydrocarbons by catalytic dehydrogenation is limited to rather low rates of conversion between 5 and 20 mole %. Accordingly the hydrocarbon rich effluent stream of the dehydrogenation zone carried by line 6 is a mixture of olefins and paraffins predominating in paraffins. The hydrocarbon effluent stream of the dehydrogenation zone 2 may be passed directly into a carbonylation zone 9 via lines 7 and 8. However, it is presently preferred to pass the hydrocarbon effluent of the dehydrogenation zone 2 through line 10 into equipment required for one or more treating steps represented by the single treating zone 11. These treating steps preferably include the selective hydrogenation of diolefins and the adsorptive removal of aromatic hydrocarbons as described below. In addition it is presently preferred to also treat the mixed hydrocarbon effluent stream by contacting with sodium, although the exact cause for this treating step being beneficial is unclear. It is postulated that this step removes small concentrations of undetermined sulfur compounds, and therefore other forms of sulfur removal such as a guard bed would be effective. Line 12 returns the treated mixture to line 8.

The carbonylation zone 9 can take many forms depending on such factors as the type of catalyst e.g. solid or homogeneous, employed in this zone. The remainder of this description of the process is presented in terms of the use of a preferred homogeneous palladium catalyst system comprising an aqueous phase together with various solvents and promoters and other compounds as described more fully below. This catalyst system is relatively easy to separate from an organic phase which contains the bulk of the feed hydrocarbons and product oxygenates.

The mixed paraffin/olefin hydrocarbon stream recovered from the dehydrogenation zone 2 is passed into the carbonylation zone and admixed with carbon monoxide entering through line 16 and recycled catalyst present in an aqueous phase carried by line 17. The contents of the reaction zone are mixed as in a CSTR maintained at carbonylation conditions to promote phase transfer between the hydrocarbon phase containing the feed stream hydrocarbons and the aqueous phase. In the embodiment being depicted, the contents of the carbonylation reaction zone also include water, which is partially consumed in the reaction, and acetone present as a solvent. Portions of the contents of the reaction zone 9 are bled off in a multi-component carbonylation zone effluent stream carried by line 18. This stream is passed into a phase separation zone 19 operated at a pressure just below that maintained in the reaction zone. This zone preferably comprises a single vapor-liquid separation vessel designed to promote the separation of the entering materials into a vapor phase removed via line 15, an liquid-phase organic (upper) phase removed via line 20 and the aqueous (bottom) phase of line 17. The composition of these streams will, of course, depend on the catalyst and solvent compositions.

The vapor phase stream of line 15 is an admixture composed mainly of unreacted carbon monoxide but also containing lesser amounts of formic acid, and acetone. It is admixed with the carbon monoxide feed stream of line 13 and a solvent (acetone) recycle stream of line 14 and then passed into the carbonylation reactor through line 16. The aqueous liquid phase withdrawn through line 17 will contain acetone, formic acid, catalyst promoter, water and dissolved catalyst plus small amounts of feed olefin and product acid. While referred to herein as the aqueous phase, it is noted that the concentration of water will be less than that of formic acid and acetone, and this phase is therefore also referred to herein simply as the bottom phase. The composition of the two liquid phases will vary with the conversion achieved in the carbonylation reactor. The "hydrocarbon" or upper liquid-phase stream is removed through line 20 and passed into a stripping column 21, which forms the beginning of the product recovery zone of the depicted process. It is anticipated that other forms of product recovery could be employed at this point in the process, but at the present time fractional distillation is preferred due to the large difference in volatility between the unreacted feed stream hydrocarbons and the product carboxylic acids. The materials passed into the fractionation column 21 are separated into a net overhead stream comprising the acetone solvent and formic acid and a net bottoms stream comprising the unreacted hydrocarbons and product acids.

In the embodiment shown in this Figure the bottoms stream of column 21 is passed into a catalyst recovery zone in which it is water washed to recover catalyst components such as the catalyst itself and inorganic promoters. This serves to recover these materials for reuse in the process and will reduce their concentration in the acid-containing product stream. This step is not necessary with all catalyst systems, and water may not be an appropriate solvent for all catalyst components. For example, tri phenyl phosphine is not soluble in water. In an alternative mode of operation the solvent used in the reaction zone could be used to wash catalyst components from the product stream. In the water wash system shown in the figure the bottoms stream of line 22 is passed into a water wash column 23 in which it rises countercurrent to a descending stream of water charged to the tower via line 25. The contacting within the column transfers water soluble compounds into the water, which is removed in line 27 and passed into a water stripping column 28. This column is operated to drive most of the water overhead leaving a small net bottoms stream having an enhanced concentration of the recovered water soluble compounds. This bottoms stream is removed via line 29 and recycled to the reaction zone 9. The make-up water stream charged to the process enters via line 26 and provides the water removed in line 29, which supplies the water consumed in the carbonylation reaction and lost by solution. It may not be possible to reuse the recovered components of line 29 in the reaction zone and this stream may instead be passed into a palladium recovery zone or into a catalyst regeneration zone. This is based upon the observation that removing the palladium-containing catalyst component from an environment which also contains a substantial carbon monoxide concentration tends to deactivate the catalyst.

The water washed bottoms stream of the first column is then passed into a second fractional distillation column 30 via line 24. The second column splits the entering admixture to produce a net overhead stream rich in the hydrocarbons present in the effluent of the carbonylation zone. In the embodiment being depicted this stream comprises mainly paraffinic hydrocarbons, but it also contains any unreacted olefinic hydrocarbons. This stream is preferably recycled to the dehydrogenation zone 2 via line 4. The net bottoms stream of the second column 30 comprises the product acid(s) and is removed through line 32. This entire stream may be drawn off the process through line 33 if desired. Alternatively all or a portion of the bottoms stream may be processed within downstream sections of the process. For instance, a portion of the bottoms stream may be diverted into line 34 and passed into a hydrogenation zone 36. In this zone hydrogen from line 5 recovered from the dehydrogenation zone may be used to hydrogenate the acid(s) to a product long chain alcohol(s) of corresponding structure to form an alcohol product stream removed from the process via line 37. The alcohols may be recovered as a product or further converted as by reaction with ethylene oxide. If the production of alcohols is not desired then the entire acid product stream may be passed through line 35 into a conversion zone 38 wherein the acids are, for example, converted to a soap by reaction with sodium hydroxide from line 39. This step will lead directly to a soap product removed from the process through line 40.

Figure 2:
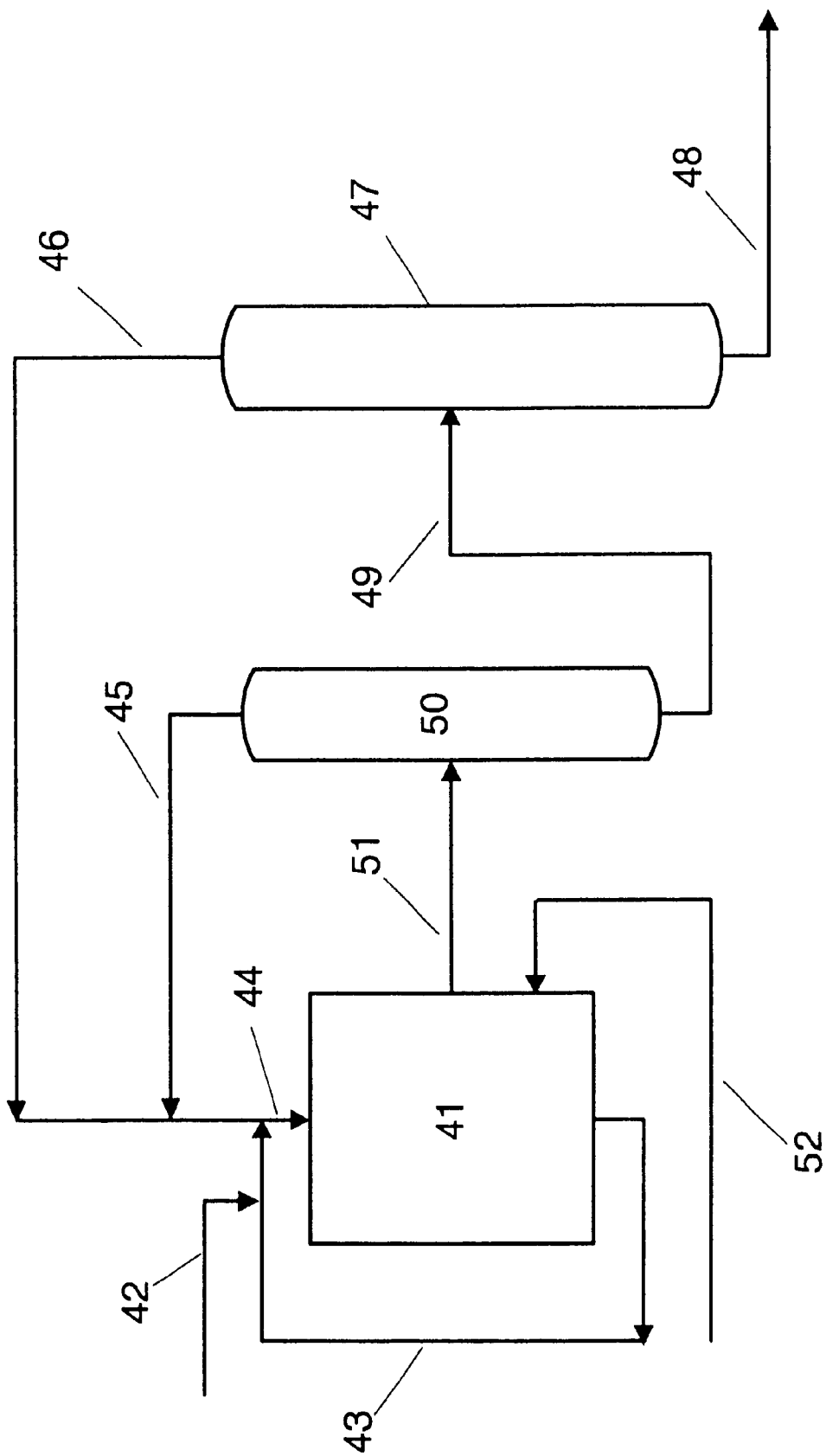
FIG. 2 is a simplified flow diagram showing use of an alternative carbonylation reactor configuration and product recovery sequence used to produce carboxylic acids from a high purity olefin feed stream.

FIG. 2 is a very simplified flow diagram presenting the major flows in the carbonylation reaction zone 41 and product recovery section arranged according to a preferred embodiment of the invention. This diagram is representative of the flows expected with a "loop venturi" type reactor. Such a reactor does not require the effluent separation vessel 19 of FIG. 1 as two liquid phases are maintained within the reactor. In this embodiment of the invention a hydrocarbon feed stream containing the feed olefin(s) enters the process via line 42 and is admixed with a larger recycle stream carried by line 43. When operated with a preferred catalyst system, e.g. one comprising palladium, imidazole, acetone and lithium iodide, the recycle stream will comprise the multi-component homogeneous catalyst, the solvent, water (or other hydroxyl providing compound such as methanol), additives such as formic acid and minor amounts of product acids and feed hydrocarbons. This admixture passes through line 44 to an eductor located within the reaction zone 41. The eductor admixes this liquid with vapor phase material present in the top portion of the reaction zone and discharges the resulting two-phase mixture into a large chamber in a lower portion of the reaction zone. The reaction forming the product acids begins upon the admixture of the olefin, carbon monoxide, water and catalyst system. The vapor-phase material contains carbon monoxide derived from a continuous carbon monoxide feed stream charged to the reaction zone 41 via line 52. The flow rate of the carbon monoxide feed stream is controlled on the basis of the pressure within the reactor, although it could be based upon a measurement of the carbon monoxide concentration in a vapor filled upper portion of the reactor zone 41.

The lower portion of the venturi reactor of the reaction zone contains a body of liquid. The reactor is preferably designed to allow the liquid phase compounds present in the reactor to separate into two phases despite the admixture occurring in the reactor due to the downward flowing stream of reactants from line 44. The remaining unreacted olefin(s) of the feed stream of line 42, and any paraffinic hydrocarbons in the feed stream, will concentrate into an upper hydrocarbon phase. The product carboxylic acid will also tend to concentrate into this phase. The catalyst components and remaining water will concentrate in a denser phase collected in the bottom of the reactor. The reactants, the products and the catalyst system adjuvants such as formic acid and solvent will however partition themselves between both phases. This division has been found to be dependent on multiple factors including the identity of the feed olefins, presence of paraffins in the feed, temperature and the degree of olefin conversion achieved in the reaction zone.

A continuous stream of the upper phase comprising the residual feed hydrocarbons, solvent, formic acid and product acids is withdrawn from the reaction zone 41 through line 51 and passed into a first fractionation column 50. This first column is designed and operated to separate the entering compounds to produce a net overhead stream comprising the solvent and formic acid and a net bottoms stream comprising residual olefin, paraffin from the feed stream and product acids. The overhead stream is recycled to the reaction zone 41 by admixture into the feed/recycle stream. The bottoms stream is passed into a second fractional distillation column 47. It is therein split into an overhead fraction comprising the great majority of the unreacted olefins and any paraffins carried by line 46 and a bottoms stream carried by line 48 comprising the great majority of the product acids. The unreacted olefins of line 46 are preferably recycled to the reactor, but a portion may be drawn off to prevent build up of paraffins and other compounds in the boiling point range of the olefins. If the feed stream of line 42 is recovered from the effluent of a dehydrogenation zone, then the contents of line 46 will normally have a low concentration of olefins and will be recycled to the dehydrogenation zone.

One embodiment of the subject invention can accordingly be characterized as a process for the production of oxygenated hydrocarbons which comprises passing a feed stream comprising a mixture of different acyclic paraffinic feed hydrocarbons having carbon numbers above 6 into a dehydrogenation zone operated at dehydrogenation conditions and converting a fractional portion of the entering paraffinic hydrocarbons into olefinic hydrocarbons of the same carbon number as the corresponding feed hydrocarbons to form a dehydrogenation zone effluent stream comprising a mixture of olefinic and paraffinic hydrocarbons; passing at least a portion of said dehydrogenation zone effluent stream, carbon monoxide and water into contact with a homogeneous carbonylation catalyst system comprising $Pd(PPh_3)_2Cl_2$, or $Pd(Im)_4Cl_2$ formic acid and LiI in a carbonylation zone operated at carbonylation conditions and converting at least a portion of said olefinic hydrocarbons to carboxylic acids, and recovering a product stream comprising carboxylic acids and paraffinic hydrocarbons from the carbonylation zone; passing said product stream into a fractional distillation zone in which the product stream is separated into at least a hydrocarbon recycle stream comprising paraffinic hydrocarbons and an acid stream comprising acyclic carboxylic acids; recycling the hydrocarbon recycle stream to the dehydrogenation zone; and, withdrawing the acid stream.

No structural change occurs in the underlying hydrocarbon during the carbonylation reaction. The desired size, and structure of the desired olefin(s) feed component is therefore set by the desired structure and size of the product oxygenates. For instance, if a branched chain organic acid is desired then the feed olefin must have the corresponding branched chain structure. Likewise if a straight chain alcohol is the desired end product of the process then a straight chain olefin is the desired feed. The location of the carbonyl group in the product acid, or corresponding group in other products, may vary from the location of the double bond in the feed olefin. It is postulated this may be due to the metal component of some carbonylation catalyst compositions promoting the isomerization of the double bond.

While the olefin feed stream can be rich or even highly pure in one particular olefin, it is anticipated that the olefin feed stream will normally comprise a mixture of isomers of an olefin or of several different olefins having different molecular weights and/or structures. For instance, a preferred source of olefins is the dehydrogenation of paraffinic hydrocarbons obtained from petroleum by adsorptive separation from a stream of the appropriate molecular weight hydrocarbons. This is commonly done in the production of linear alkyl benzene (LAB) used in the production of detergents. Paraffins having a range of carbon numbers, such as $C_9$ to $C_{12}$, $C_{11}$ to $C_{14}$ or $C_{10}$ to $C_{13}$ paraffins, can be extracted from a hydrotreated kerosene fraction and charged to the dehydrogenation zone of the process. The selectivity of the adsorption zone may be controlled by choice of adsorbents and operational technique to provide recovered paraffins which are either straight chain paraffins or a mixture of straight chain and slightly branched paraffins such as mono-methyl paraffins.

Alternatively, straight chain paraffins recovered by extraction can be fed to a skeletal isomerization zone in which the straight chain paraffins are converted into isoparaffins with various degrees of branching. The desired structure for the feed paraffin is set by the desired structure of the intended product oxygenate. The adsorptive recovery of the paraffins and any subsequent isomerization steps are therefore also set by this preference. The isomerization steps may include selective adsorptive separation steps which separate the effluent of an isomerization reactor into product and recycle fractions. The feed paraffins may be chosen from such representative compounds as heptane, n-octane, n-nonane, 2-methyl nonane, 3-methyl nonane, 2,3-dimethyl pentane, 2,3,6-trimethyl heptane, 2-methyl, 3-propyl decane, etc.

The olefinic substrate acted upon in the carbonylation reaction may be a side chain of a cyclic compound, with the cyclic portion of this compound being either saturated or aromatic in nature. To produce the presently desired detergent precursors it is preferred that the alkyl side chain is at least about 5 carbon atoms long. Therefore the "feed olefin" charged to the process can be a $C_{11}$-plus mono-branched alkenyl aromatic hydrocarbon. The subject carbonylation can be applied to branched aromatic hydrocarbons having a shorter carbonylizable alkene side chain or multiple alkene side chains if so desired.

As already mentioned, the preferred method of producing the olefins consumed in the subject process is by the dehydrogenation of the corresponding paraffin. The dehydrogenation is performed by bringing the paraffins into contact with a suitable dehydrogenation catalyst maintained at dehydrogenation conditions. This conversion step is well known in the art and widely practiced in large scale commercial process units to produce aliphatic olefins.

The feed olefins may be alpha olefins or internal olefins or a mixture of both. Suitable olefins for consumption in the subject process may be produced by means other than dehydrogenation. One such alternative is the oligomerization of small olefins such as ethylene, propylene or butene or other sequential reactions which produce aliphatic alkenes. For instance, the production of butane oligomers from Fisher-Tropsch olefins is described in U.S. Pat. No. 5,994,601 and from field butanes in U.S. Pat. No. 5,998,685. The production of linear olefins by oligomerization is also described in U.S. Pat. Nos. 4,689,437 and 4,716,138 which are incorporated herein for their teaching regarding this technology. The olefins may be considered as only one of the several possible substrates of the carbonylation reaction. Other alternative hydrocarbon feed reactants (substrates) which could be consumed instead of an olefin include various linear alcohols.

As also mentioned above, the effluent of a paraffin dehydrogenation zone will normally contain a small amount of byproducts including aliphatic diolefins and aromatic hydrocarbons. While the conversion of diolefins into acceptable di-acids in the carbonylation zone or into unsaturated acids are alternative embodiments of the subject process, it is presently preferred to remove both diolefins and aromatics from the effluent of the dehydrogenation zone prior to its passage into the carbonylation reaction zone in order to produce high purity saturated aliphatic acids. Aromatic hydrocarbons are relatively unaffected by the carbonylation reaction and would build up in a recycle stream if not otherwise removed as via a drag stream. Unfortunately, drag streams also remove desired material and therefore add to the cost of the process. It is therefore preferred to remove the diolefinic hydrocarbons from the feed by selective hydrogenation and to then remove the aromatic hydrocarbons by adsorption. These steps may be performed as described in U.S. Pat. No. 5,300,715. The removal of diolefinic hydrocarbons may not be necessary if the products formed from them in the carbonylation reaction are acceptable or desirable products of the process or if the specific diolefins do not react twice with the carbon monoxide.

It is presently preferred to pass the olefin feed stream to the carbonylation zone through a desulfurization zone, especially if it is formed in a dehydrogenation zone. In a small scale unit such as a pilot plant this zone can take the form of a sodium treater in which the liquid phase hydrocarbons contact sodium metal. In a large scale unit a guard bed system allowing continuous treatment would be preferred. The hydrocarbon feed would be contacted at suitable liquid phase adsorption conditions such as a temperature of about 20–40° C. with a particulate form adsorbent such as activated alumina or a large pore alumina supporting for example 1–3 wt % nickel or copper. It is presently preferred to reduce the sulfur concentration below 2 ppm, more preferably 2 ppm (mole) and most preferably as low as possible. The apparent sensitivity of the preferred catalyst systems to sulfur is surprising since it does not appear to be reported in the art. It is also surprising that sufficient sulfur to deactivate the catalyst during a batch reaction was apparently present in the mixed paraffin-olefin dehydrogenation zone effluent since this is a highly refined material derived from material which is highly desulfurized before the adsorptive separation step which provides the paraffins. The adsorption step itself would reduce the sulfur level in the paraffins as would various other adsorbents used in this process as guard beds. Finally, the dehydrogenation zone effluent had been subjected to hydrotreatment to remove diolefins. However, it is also noted that sulfur is added at a very low level during the selective diolefin hydrogenation step, and this may have caused the feed olefins to be contaminated.

Operating conditions suitable for the carbonylation reaction zone of the subject process include a temperature of about 25 to 200° C., preferably from 100 to 170° C., and a pressure as required to maintain at least a portion (greater than 50 mole %) of the feed hydrocarbon present as a liquid. Significantly elevated pressures on the order of about 20 to 200 bar are often employed, with the subject carbonylation reaction zone preferably being operated at a pressure of about 60 to 100 bar. The pressure is not believed to have significant effect on the performance of the process other than by its impact on the solubility of the carbon monoxide in the liquid phases. Some catalysts are known to be sensitive to changes in pressure and it is therefore preferred to minimize pressure changes within the process. Specifically, it is preferred that no significant reduction in pressure occur while a significant amount of catalyst is present. The first separation, really a decantation, should therefore be performed at a pressure near that maintained in the reaction zone.

Oxygen and other gases such as hydrogen and nitrogen may be present in the carbon monoxide feed gas as an impurity. The reaction zone is preferably operated with a minimum practical concentration of oxygen. Besides treating the feed gas, a small purge stream may be removed from the reaction zone on a continuous or periodic basis as necessary to control the concentration of undesired gaseous compounds such as methane, carbon dioxide and hydrogen.

Water or a light alcohol, such as methanol or ethanol, is charged to the reaction zone as a hydroxyl source. Water is preferred due to its low cost. Methanol is the preferred alcohol as it can lead to the production of methyl esters. This reactant and the carbon monoxide should be of high purity and substantially free of materials detrimental to the catalyst. Inert gases may be present in the carbon monoxide.

It is generally preferred that the carbonylation reaction zone is operated with a water concentration significantly above the olefin concentration in the reaction zone. The water concentration or charge rate, can therefore range from about 100 to 1000 mole % of the olefin concentration, with a concentration between 100–500% being preferred. Unless otherwise stated, this and other statements regarding the concentration of reaction components or adjuvants are in terms of their concentration in the mixed liquid phase present in the reaction zone. The preferred water concentration is equivalent to about 2–7 vol. %. The concentration of carbon monoxide in the reaction zone is more difficult to specify due to the tendency of the CO to be concentrated in the gas phase, from which it transfers to the liquid phase. The molar ratio of carbon monoxide to feed olefin in the total contents of the reaction zone is preferably with in the broad range of from about 1:1 to about 10,000:1. More preferably this ratio is in the range of from about 10:1 to about 10,000:1. The carbon monoxide concentration can also be measured in terms of pressure, with a carbon monoxide partial pressure of about 8 MPa being preferred.

As the references cited above illustrate, there are a significant number of alternative carbonylation catalysts including both heterogeneous and homogeneous catalysts. Many of these catalysts are complexes containing a metal such as nickel, cobalt, rhodium, platinum or palladium and one or more associated ligands. The palladium-phosphine complexes e.g. Pd-triphenylphosphine of the Fenton paper are examples of this as is the ligand stabilized platinum(II) group 4B metal halide complex of Knifton. A workable process can be created using catalysts of this nature. However, it is preferred to employ a catalyst system comprising palladium and an imidazole complex. Imidazole ($C_3N_2H_4$) is a five member ring structure having two nitrogen atoms in the ring. Its structure is shown in U.S. Pat. No. 6,127,574. A representative catalyst of this type is represented by the formula $Pd(Im)_4Cl_2$ where Im stands for imidazole. Substituted imidazoles may be employed. For instance, 2-methylimidazole, 2-ethylimidazole and benzimidazole appear to give equivalent performance to unsubstituted imidazole.

The amount of metal, preferably palladium, and less preferably rhodium in the catalyst system is another important variable. The amount of active metal can be in the broad range of about 50-wt. ppm to about 1200 ppm or higher, with the upper limit of metal concentration being set by metal solubility. This concentration is based upon the volume of the liquid phase present in the reaction zone which has the highest catalyst concentration rather than the entire contents of the reaction zone. If there is only one phase then the volume of this phase is used. The required metal concentration in the reaction zone is highly dependent on the desired reaction zone volume as activity is related to metal concentration. That is, the desire to use a smaller reactor leads to a need for a higher metal concentration.

The catalyst systems employ a component referred to as a "solvent". The presence of a solvent in the reaction zone tends to improves the mutual solubility of the reactants and catalyst. The solvent may also increase the solubility of $Pd(PPh_3)_2Cl_2$ or improve the solubility of $Pd(Im_4)Cl_2$ and reactants. Compounds useful as solvents include paraffins, ketones having less than seven carbon atoms and monocyclic aromatic hydrocarbons, such as toluene or a xylene. Methyl ethyl ketone and methyl isobutyl ketone are examples of the $C_7$ ketones. Preferred solvents are undecane, acetone and o-xylene, with acetone and o-xylene being highly preferred.

It has been discovered that the choice of solvent has a significant impact on performance of the overall reaction. It appears the use of acetone as a solvent can increase the rate and/or extent of the olefin's reaction in the carbonylation reaction zone, especially when the feed olefin is a mixture comprising internal olefins. A disadvantage to the use of acetone is that it is a solvent for the desired product acids and therefore tends to increase the concentration of the product acid in the bottom phase of the reaction zone. This in turn increases the amount of product which is in the reactor recycle loop. The use of xylene as a solvent reduces this presence of product in the bottoms phase. It therefore reduces the amount of liquid being recycled and eases the separation of the product acids. The choice of solvent can therefore have an impact on the design and operation of a commercial scale process. For instance, it has been discovered that at higher conversion rates, e.g. over 90 mole percent conversion of a high purity olefin to acid, the liquid phase contents of the reaction zone tend to form a single phase. Therefore with a pure olefin feed the initial phase separation into a bottom recycle phase and an upper product-containing phase cannot be performed in a phase separation vessel and the entire contents of the carbonylation reactor must be fractionated. Other changes could, of course, be made to hold down conversion and produce two phases. Conversely, the use of a solvent which promotes a higher conversion can be useful when processing a feed stream containing a significant amount of internal olefins, which react more slowly than α-olefins.

It has been observed that the addition of o-xylene or acetone will surprisingly increase the conversion of internal olefins to acids. Acetone seems to provide the best increase in conversion. It is postulated this may be the result of the solvent facilitating the isomerization of the internal olefins to the more reactive alpha olefins by the carbonylation catalyst. An alternative postulation, based upon the presence of all possible internal acids in the product, is that the solvent promotes internal carbonylation. The use of o-xylene or another suitable aromatic hydrocarbon is therefore preferred when the conversion rate is otherwise less than desired. The xylene can be used in admixture with another hydrocarbon added as a solvent. When the feed stream to the carbonylation zone is essentially free (less than 2 mol-%) of paraffins, then the solvent phase can be a mixture of a xylene and an added paraffin, such as a mixture of o-xylene and decane or undecane. In such instances the paraffin(s) is preferably the same carbon number as the olefin(s) in order that any paraffin exiting the reaction zone is recycled with unconverted olefins.

It has been noted in the literature that a moderate amount of an organic acid can be present in the reaction zone. It is preferred to operate at a low pH below 6.0. The art has suggested the use of acetic acid or even the product acid when the rate of the reverse reaction is minor. When the catalyst system contains $Pd(Im)_4Cl_2$ it is preferred to maintain a concentration of a small chain organic acid in the reactor equal to about 1 to about 15 mole percent of the olefin in the reaction zone. The term small chain organic acid is intended to indicate an organic acid containing a total of less than about 6 carbon atoms per molecule. A preferred small chain organic acid is formic acid. For the $Pd(PPh_3)_2Cl_2$ type catalyst systems there are a number of promoters which do not require formic acid.

Another component of the catalyst system of the subject process is a "catalyst promoter" which is sometimes also referred to as a "co-catalyst." These are normally inorganic salts such as lithium bromide, lithium iodide, tin chloride, zirconium chloride or iron chloride. Lithium iodide is the preferred catalyst promoter for use in the subject process when the catalyst system comprises imidazole. The catalyst promoter may be present in a wide range of concentrations, most easily expressed in terms of the mole ratio of promoter to catalyst in the reaction zone. This ratio may be within the broad range of from about 0.1:1.0 to 10,000:1.0 or more. Ratios in the range of 10: to 100:1.0 appear suitable. In this context the term catalyst refers to the metal containing complex.

Representative examples of the preferred catalyst systems therefore include (1) $Pd-Im_4Cl_2$ plus LiI promoter plus a small chain organic acid plus 0-xylene as a solvent. (2) $Pd-Im_4Cl_2$ plus LiI plus formic acid with acetone as solvent and (3) $Pd-Im_4Cl_2$ plus LiI plus formic acid and o-xylene as solvent. Other catalyst systems which can be employed in the subject process are (1) $Pd(PPh_3)_2Cl_2$, formic acid, and LiI with acetone solvent and (2) $Pd(PPh_3)_2Cl_2$ with formic acid and $ZrCl_4$. $PPh_3$ refers to tri phenyl phosphine (TPP).

While certain homogeneous catalysts are presently preferred, the broader process embodiments of the invention can be practiced with other catalysts including heterogeneous catalysts. In this regard it is noted that the use resin catalysts containing imidazole has been described in the literature. The choice of reactor type is greatly influenced by the type of catalyst employed in the process. With a heterogeneous catalyst a fixed bed of catalyst is preferred at this time in order to lessen catalyst attrition as can occur with a moving bed of catalyst. A moving catalyst system such as the circulating catalyst referred to in previously cited U.S. Pat. No. 5,981,796 would allow on stream replacement of catalyst should this be necessary.

A number of different reactor systems have been employed to perform reactions involving homogeneous catalysts. These include simple stirred tank reactors (CSTR), several tanks in series. The use of such reactors is not preferred due to problems with potential leakage at the seals on the long shafts of the rotating mixers commonly employed to admix the reactants and catalyst. The loop-venturi reactors referred to above are preferred. These reactors are described in a paper *Loop Venturi Reactor—A Feasible Alternative to Stirred Tank Reactors?* By L. van Dierendonck et al, *Ind Eng Chem. Res.* 1998, 37, 734–738.

It is preferred that the entire olefin containing feedstream is passed into a single carbonylation reaction zone. However, this reaction zone may employ more than one reactor in series flow to increase per pass conversion or increase selectivity and reduce overall reactor volume. The two reactors may be different in kind, e.g. a fixed bed first stage followed by a homogeneous second stage reactor, or may differ in reaction conditions, carbon monoxide concentration, catalyst or solvent which is employed. Further, the addition of a co-reactant, either water or carbon monoxide may be staged within a single reactor or between sequential reactors. A further process variant comprises the addition of different co-reactants in the different reactors.

As mentioned above, numerous unreactive compounds and by-products may accumulate in the process. It is therefore preferred to continuously remove small portions of the vapor and bottom liquid from the reaction zone contents as drag streams. These streams can be processed to recover compounds which may be returned to the reaction zone or totally removed from the process. Alternatively the drag streams may be passed through purification zones, such as an adsorption, stripping or flash zone, which will reduce the concentration of one or more components of the drag stream and then the entire purified drag stream may be returned to the process. A drag stream and corresponding makeup stream may be needed to maintain the activity of the catalyst. It is believed a palladium-phosphine type catalyst which has been deactivated, as by depressurization, may be regenerable. A regeneration method for catalysts of this type is described in U.S. Pat. No. 3,928,231, which is incorporated herein for this teaching.

The recovery techniques discussed above focused upon using the different volatilities between the product acids and the unreacted hydrocarbons present in the carbonylation zone effluent stream. Thus, emphasis was placed upon fractional distillation. Other methods can be used as alternative methods of recovering the acids. For instance, a chemical technique focusing on the significantly different natures of the acids and the unreacted paraffins/olefins can be employed. One such technique is to precipitate the acid as a soap. This technique comprises contacting the mixed hydrocarbon/acid mixture (upper phase) with sodium hydroxide at ambient conditions to neutralize the acid and form a salt. Alternative techniques for recovery of the product include extraction of the acids into a suitable solvent or crystallization.

EXAMPLE 1

A feed mixture comprising 5.6 ml of 1-dodecene was placed into a cylindrical metal reaction vessel together with 4.5 ml of o-xylene solvent, 6.75 ml of formic acid, 2.25 ml of water and $1.48 \times 10^{-4}$ mol of $Pd(Im)_4Cl_2$ catalyst and 1.31 gm of lithium iodide promoter. The vessel was sealed and then pressurized with carbon monoxide to 8.0 MPa. The vessel had an internal volume of 150 cc, which provided ample room for the carbon monoxide after receiving the liquid phase materials. The contents were subjected to mixing by rotating the vessel while it was maintained at a temperature of 130° C. for a period of three hours. The vessel was then cooled to room temperature and its contents removed for analysis. Analysis of the products indicated a conversion rate of 47% and a selectivity of 86% to carboxylic acid.

EXAMPLE 2

The procedure of Example 1 was repeated except that the solvent was 18 ml of acetone and the feed olefin was contained in 5.6 ml of a $C_{10}$–$C_{13}$ hydrocarbon mixture collected from the effluent of a paraffin dehydrogenation zone. This mixture contained 88.9 mole % normal paraffins, 7.0% normal olefins and 4.1% branched olefins and paraffins, and was intended to simulate the effluent of a dehydrogenation zone. The duration of the test was 9 hours.

The liquid remaining after the reactants were cooled and separated from gases was analyzed, indicating a conversion of 67%. Analysis showed a complete distribution of internal acids.

EXAMPLE 3

In an experiment intended to investigate the feasibility of employing phase separation as the first step in catalyst and product recovery, the composition of the total liquid recovered from the vessel in the two tests described above was simulated by admixing equivalent amounts of the same components. These admixtures were allowed to separate into two phases, which were analyzed to have the weight % compositions given in Table 1. This simulates the separation of the carbonylation reactor effluent for the cases of 90% conversion of pure 1-dodecene with o-xylene solvent and 95% conversion of the dehydrogenation zone effluent olefins with acetone solvent, respectively.

TABLE 1

|  | Olefin Feed (Ex. 1) | | Mixed Feed (Ex. 2) | |
| --- | --- | --- | --- | --- |
|  | Upper Phase | Lower Phase | Upper Phase | Lower Phase |
| Solvent | 42 | 0.5 | 11.1 | 53.5 |
| HCOOH | 2.4 | 75.8 | 2.9 | 26.7 |
| Dodecene | 4.9 | 0.25 | 0.2 | 0.015 |
| Undecane |  |  | 81.7 | 1.5 |
| Tridecanoic acid | 49.8 | 0.3 | 2.2 | 0.8 |
| Water | remainder | remainder | remainder | remainder |

EXAMPLE 4

The procedure of Example 1 was again repeated except that the solvent was 18 ml of acetone and the catalyst was $1.80 \times 10^{-5}$ mol of $Pd(TPP)_2Cl_2$ and the promoter was 0.322 gm of $ZrCl_4$, the vessel was pressurized to 10 MPa with CO and heated to only 125° C. for three hours.

The liquid remaining after the reactants were cooled and separated from gases was analyzed, indicating a conversion of 80% and a selectivity of 91%.

EXAMPLE 5

A carbonylation reaction was performed using the above described techniques and a $C_{10}$ to $C_{13}$ paraffin/olefin mixture recovered from the effluent of a paraffin dehydrogenation zone, and the liquid phase mixture recovered from the pressure vessel was allowed to separate into two liquid phases. The upper phase, which contained the product acids, was separated from the lower phase, twice washed with water with 50 cc of water and then with 10% aqueous KOH solution. The aqueous layer, which contained the desired compounds, was removed and washed with 20 cc. of hexane to remove any entrained organics such as the solvent and then reacted with HCl until slightly acidic. The desired compounds were extracted with 50 cc of hexane, and the phases were separated. The organic layer was washed with 20 cc of water, and then the nonproduct organics were driven off by evaporation promoted by application of a vacuum at 40–50° C. until a constant weight was obtained. The final product contained fatty acids produced in the process.

EXAMPLE 6

Again using the same equipment and procedure as Example 1 a test was performed using 0.10 gm of Pd $(PPh_3)_2Cl_2$, 6.75 ml of formic acid and 1.31 gm of LiI promoter as the catalyst components. The feed was the $C_{10}$–$C_{13}$ of Example 2. The test was performed at 150° C., with 28 ml of acetone added as the solvent. Analysis of the product liquid showed an olefin conversion rate of 98% at a selectivity of 99.6%.

EXAMPLE 7

The experiment of Example 1 was repeated but using 2.42 gm of HI as the promoter and 4.5 ml of acetic acid instead of the formic acid. 4.5 ml of o-xylene was employed as the solvent. The feed was 5.6 ml of 1-dodecene. Conditions were a temperature of 185° C. and a pressure of 8 MPa. Analysis of the recovered liquid product indicated 93% conversion and 16% selectivity to monocarboxylic acids.

EXAMPLE 8

The experiment of Example 1 was repeated but the solvent was changed to a mixture of 18 ml of acetone and 5.26 ml of undecane. Analysis of the recovered liquid product indicated 86% conversion of the feed olefin at 96% selectivity.

EXAMPLE 9

The experiment of Example 1 was repeated using 0.1 gm of Pd TPP and 1.31 gm of LiI as promoter. 52.6 ml of undecane was employed as the solvent and 6.75 ml of formic acid was added to the liquid phase. Analysis of the recovered liquid product indicated a conversion of 51% at a selectivity of 99%.

EXAMPLE 10

The experimental procedure of Example 1 was repeated using 0.1 gm of Pd TPP with 1.61 gm of $SnCl_2$ as the promoter. No acid was added, and 18 ml of acetone was added as the solvent. Analysis of the recovered liquid product indicated a conversion of 27% at a selectivity of 96%.

EXAMPLE 11

The experimental procedure of Experiment 1 was repeated using 0.1 gm of Pd TPP and 0.78 gm of a mixture of $ZrCl_4$ and $SnCl_2$ as promoter. The solvent was 18 ml of acetone. No light acid was added. Analysis of the recovered liquids indicated a conversion of 27% at a selectivity of 96%.

As mentioned above, a primary envisioned use of the acid products of the subject process is in the production of detergents and soaps including dish washing detergents, hand soap and laundry detergents. The acids are normally first converted into other synthetic detergent intermediates, such as primary or secondary alcohols. The conversion of acids to alcohols can be by mild hydrogenation over a heterogeneous catalyst. The alcohols can then be reacted multiple molecules of ethylene oxide to manufacture linear alcohol ethoxylate nonionic surfactants. Many important surfactants are sulfonates or sulfates e.g. sodium lauryl sulfate, are built upon these same intermediates as by sulfonation of an alcohol or acid. Many of the household detergents and cleaners derived from these intermediates are actually formulated from several active surfactants plus other materials, such as suds suppressors, builders or enzymes which impart improved cleaning characteristics to the final products. Further information on the formulation of such household products from acids produced by the subject process may be obtained form U.S. Pat. Nos. 5,736,503 and 6,020,303 and from WIPO publication WO 99/07656. Information on detergent production is also available from "Detergent Manufacture Including Zeolite Builders and Other New Materials," Ed. Siltig, Noyes Data Corp., New Jersey, USA, 1979. Sulfonation is described in more detail in "Sulfonation Technology in the Detergent Industry," W. H. deGroot, Kluwer Academic Publishers, Boston, USA, 1991.

What is claimed:

1. A continuous process for the production of oxygenated hydrocarbons which comprises:

(a) passing a feed stream comprising at least two different paraffinic hydrocarbons, each having a carbon number above 6, into a dehydrogenation zone operated at dehydrogenation conditions and converting a least a portion of the entering paraffinic hydrocarbons to olefinic hydrocarbons of the same carbon number to form a dehydrogenation zone effluent stream comprising a mixture of olefinic and paraffinic hydrocarbons;

(b) passing at least a portion of the hydrocarbons of said dehydrogenation zone effluent stream, carbon monoxide and a hydroxyl-supplying feed compound chosen from water and a light alcohol into contact with a homogeneous carbonylation catalyst in a carbonylation zone operated at carbonylation conditions and converting at least a portion of said olefinic hydrocarbons to desired carbonylation products, and recovering a process stream comprising carbonylation products and paraffinic hydrocarbons from the carbonylation zone;

(c) passing said process stream into a fractional distillation zone in which the process stream is separated into at least a hydrocarbon recycle stream comprising paraffinic hydrocarbons and an oxygenate stream comprising carbonylation products recycling the hydrocarbon recycle stream to the dehydrogenation zone; and, (d) recovering the carbonylation products.

2. The process of claim 1 wherein the dehydrogenation zone effluent stream is treated by a series of steps which comprises contacting the effluent stream with sodium prior to passage into the carbonylation zone.

3. The process of claim 1 wherein the dehydrogenation zone effluent stream is treated by selective diolefin hydrogenation.

4. The process of claim 1 further characterized in that the fractional distillation zone comprises a first fractionation column, which receives said process stream, a second fractionation column and an intermediate water wash zone in which a bottoms stream recovered from the first fractionation column is contacted with water to form a wash water stream comprising a carbonylation catalyst component, and the water wash stream is concentrated in a water stripping column and then passed into the carbonylation zone.

5. The process of claim 1 further characterized in that the carbonylation catalyst is a homogenous system which comprises palladium and imidazole.

6. The process of claim 5 further characterized in that the homogeneous catalyst system also comprises formic acid.

7. A process for the production of oxygenated hydrocarbons which comprises:
(a) passing a feed stream comprising a mixture of different paraffinic feed hydrocarbons having carbon numbers above 6 into a dehydrogenation zone operated at dehydrogenation conditions and converting a fractional portion of the entering paraffinic hydrocarbons into olefinic hydrocarbons of the same carbon number as the corresponding feed hydrocarbons to form a dehydrogenation zone effluent stream comprising a mixture of olefinic and paraffinic hydrocarbons;
(b) passing said dehydrogenation zone effluent stream, carbon monoxide and water into contact with a homogeneous carbonylation catalyst in a carbonylation zone operated at carbonylation conditions and converting at least a portion of said olefinic hydrocarbons to carboxylic acids, and recovering a product stream comprising carboxylic acids and paraffinic hydrocarbons from the carbonylation zone;
(c) passing said product stream into a product recovery zone comprising a fractional distillation zone to yield at least a hydrocarbon recycle stream comprising paraffinic hydrocarbons and an acid stream comprising carboxylic acids originally present in the product stream;
(d) recycling the hydrocarbon recycle stream to the dehydrogenation zone; and,
(e) withdrawing the acid stream from the process.

8. The process of claim 7 wherein the dehydrogenation zone effluent stream is treated by a series of steps which comprises contacting the effluent stream with sodium.

9. The process of claim 7 wherein the dehydrogenation zone effluent stream is treated by a series of steps which comprises selective diolefin hydrogenation.

10. The process of claim 7 further characterized in that at least a portion of the acid stream is passed into a hydrogenation zone in which carboxylic acids are converted to alcohols, and recovering alcohols from the hydrogenation zone.

11. The process of claim 7 wherein at least a portion of the acid stream is passed into a conversion zone in which the entering carboxylic acids are converted into a soap component.

12. The process of claim 7 further characterized in that the fractional distillation zone comprises a first fractionation column, which receives said product stream, a second fractionation column and an intermediate catalyst recovery zone.

13. The process of claim 12 further comprising the step of treating the dehydrogenation zone effluent stream by selective hydrogenation of diolefinic hydrocarbons.

14. The process of claim 12 wherein a bottoms stream recovered from the first fractionation column is contacted with water in a water wash zone to form a wash water stream comprising a carbonylation catalyst component, and the water wash stream is concentrated in a water stripping column and then passed into the carbonylation zone.

15. A process for the production of oxygenated hydrocarbons which comprises:
(a) passing a feed stream comprising a mixture of different acyclic paraffinic feed hydrocarbons having carbon numbers above 6 into a dehydrogenation zone operated at dehydrogenation conditions and converting a fractional portion of the entering paraffinic hydrocarbons into olefinic hydrocarbons of the same carbon number as the corresponding feed hydrocarbons to form a dehydrogenation zone effluent stream comprising a mixture of acyclic olefinic and paraffinic hydrocarbons;
(b) passing at least a portion of said dehydrogenation zone effluent stream, carbon monoxide and water into contact with a homogeneous carbonylation catalyst system comprising a palladium triphenyl phosphine complex or a palladium imidazole complex, formic acid and lithium iodide in a carbonylation zone operated at carbonylation conditions and converting at least a portion of said olefinic hydrocarbons to carboxylic acids, and recovering a product stream comprising carboxylic acids and paraffinic hydrocarbons from the carbonylation zone;
(c) passing said product stream into a fractional distillation zone in which the product stream is separated into at least a hydrocarbon recycle stream comprising paraffinic hydrocarbons and an acid stream comprising acyclic carboxylic acids;
(d) recycling the hydrocarbon recycle stream to the dehydrogenation zone; and,
(e) recovering acyclic carboxylic acids from the acid stream.

16. The process of claim 15 further characterized in that the contacting of the carbonylation catalyst with the dehydrogenation zone effluent stream is performed in the presence of a solvent chosen from the group consisting of monocyclic aromatic hydrocarbons and ketones.

17. The process of claim 15 further characterized in that the dehydrogenation zone effluent stream is passed through a sulfur removal zone in which the concentration of sulfur in the dehydrogenation zone effluent stream is reduced to less than 2 ppm.

18. The process of claim 15 further characterized in that recovered acyclic carboxylic acids are hydrogenated to yield acyclic alcohols.

19. A carbonylation process which comprises passing water, carbon monoxide and a $C_8$-plus aliphatic substrate chosen from the group consisting of olefins, alcohols and esters into a carbonylation reaction zone maintained at carbonylation conditions and into contact with a homogeneous carbonylation catalyst system comprising a palladium imidazole complex, an aliphatic organic acid and a solvent to produce the corresponding carboxylic acids, and recovering said carboxylic acids from the carbonylation reaction zone.

20. The process of claim 19 wherein the aliphatic organic acid present in the catalyst system is formic acid.

21. The process of claim 19 further characterized in that the $C_8$-plus aliphatic substrate is a side chain of a cyclic compound.

22. The process of claim 19 further characterized in that the carbonylation conditions include a water concentration greater than the olefin concentration.

23. A carbonylation process which comprises passing water, carbon monoxide and a $C_8$-plus aliphatic substrate chosen from the group consisting of olefins, alcohols and esters into a carbonylation reaction zone maintained at carbonylation conditions and into contact with a homogeneous carbonylation catalyst system comprising either a palladium imidazole complex or palladium triphenyl phosphine complex, an aliphatic organic acid, lithium iodide, and a solvent to produce the corresponding carboxylic acids, and recovering said carboxylic acids from the carbonylation reaction zone.

24. A carbonylation process which comprises desulfurizing a $C_8$-plus aliphatic substrate chosen from the group consisting of olefins, alcohols and esters to a sulfur content below 2 ppm; passing water, carbon monoxide and the $C_8$-plus aliphatic substrate into a carbonylation reaction zone maintained at carbonylation conditions and into contact with a homogeneous carbonylation catalyst system comprising either a palladium imidazole complex or palladium triphenyl phosphine complex, an aliphatic organic acid, and a solvent to produce the corresponding carboxylic acids, and recovering said carboxylic acids from the carbonylation reaction zone.

25. A carbonylation process which comprises passing water, carbon monoxide and a $C_8$-plus aliphatic substrate chosen from the group consisting of olefins, alcohols and esters into a carbonylation reaction zone maintained at carbonylation conditions and into contact with a homogeneous carbonylation catalyst system consisting essentially of a palladium triphenyl phosphine complex, an aliphatic organic acid and a solvent to produce the corresponding carboxylic acids, and recovering said carboxylic acids from the carbonylation reaction zone.

26. The process of claim 25 wherein the aliphatic organic acid present in the catalyst system is formic acid.

27. The process of claim 25 further characterized in that the catalyst system contains lithium iodide.

28. The process of claim 25 further characterized in that the $C_8$-plus aliphatic substrate is desulfurized to a sulfur content below 2 ppm prior to use in the process.

29. The process of claim 25 further characterized in that the $C_8$-plus aliphatic substrate is a side chain of a cyclic compound.

30. The process of claim 25 further characterized in that the carbonylation conditions include a water concentration greater than the olefin concentration.

* * * * *